United States Patent [19]

Domb

[11] Patent Number: 4,888,413

[45] Date of Patent: Dec. 19, 1989

[54] POLY(PROPYLENE GLYCOL FUMARATE) COMPOSITIONS FOR BIOMEDICAL APPLICATIONS

[76] Inventor: Abraham J. Domb, 6410 Elray Dr., Baltimore, Md. 21209

[21] Appl. No.: 142,471

[22] Filed: Jan. 11, 1988

[51] Int. Cl.⁴ ............................................. C08G 63/02
[52] U.S. Cl. .................................... 528/272; 528/296; 528/297; 528/302; 528/303; 523/113; 424/78; 424/425
[58] Field of Search ............... 528/272, 297, 302, 303, 528/296; 523/113; 424/78, 425

[56] References Cited

U.S. PATENT DOCUMENTS

| | | | |
|---|---|---|---|
| 3,978,203 | 8/1976 | Wise | 424/22 |
| 4,080,969 | 3/1978 | Casey et al. | 128/335.5 |
| 4,722,948 | 2/1988 | Sanderson | 523/11 S |

*Primary Examiner*—John Kight
*Assistant Examiner*—S. A. Acquah
*Attorney, Agent, or Firm*—Kilpatrick & Cody

[57] ABSTRACT

The present invention are highly reproducible poly(-propylene glycol fumarate) compositions having a controlled end group ratio and range of molecular weights with minimal low molecular weight and excessively high molecular weight fractions, and methods for their manufacture. These compositions, having a preferred weight average molecular weight (Mw) of between about 500 and 3000 and a number average molecular weight (Mn) of between about 300 and 2000, are especially useful in biomedical applications such as in bone cements and tissue implants or glues. In the preferred embodiment, the polymer is prepared from propylene glycol (PG) and fumaric acid (FA) by one of three methods: melt polymerization using non-volatile starting materials; step polymerization where in each step the polymer is increased by the addition of two groups to the polymer ends; or under reaction conditions maintained so that only the condensation byproduct, water, is removed during the reaction, thereby keeping the ratio between PG and FA constant. Variations of the PPF polymers include polymers with increased sensitivity to hydrolysis through incorporation of lactic acid groups into the polymer and polymers formed from maleic acid, maleic anhydride, citraconic acid or citraconic anhydride.

36 Claims, No Drawings

POLY(PROPYLENE GLYCOL FUMARATE) COMPOSITIONS FOR BIOMEDICAL APPLICATIONS

This invention includes methods for the production of highly reproducible poly(propylene glycol fumarate) compositions having improved mechanical properties and biodegradability for use in biomedical application.

Polymers and plastics are being applied in a number of areas of medicine and surgery in response to a variety of needs. Some needs emphasize permanence in the body environment. In other situations biodegradability is desirable. Biocompatibility is a consideration in all cases, although total inertness is not vital in every instance. Physical strength or resilience, permeability or diffusional transport characteristics and plasticity or formability are further considerations.

The criteria with respect to degradability vary widely according to the application. There exists at one extreme a demand for permanence, as for heart valves or pacemakers. Inbetween, a relatively non-biodegradable material such as Mylar polyester may be chosen for fabrication of a tissue-reinforcing network. At the other extreme, fairly rapid degradation may be desired. Degradable sutures are a prime example, of which polyglycolic acid has emerged as the material of choice. A related material, polylactic acid, and polyanhydrides are being used extensively as matrices for drug delivery implants providing sustained release for periods of a few days to a few weeks.

It has been postulated that polylactic acid can be used as a biocompatible implant material due to the fact that the hydrolyzed breakdown product, lactic acid, occurs naturally in the body. The fact that no foreign substance or disruptive chemical is produced appears to be of primary importance in rendering a material innocuous when implanted in the tissues.

This reasoning has led to a search for other families of polymers dissolving in the tissues to produce material normally present in the body, such as polyesters prepared from compounds in the Krebs metabolic cycle (the "critic acid cycle" or the "tricarboxylic acid cycle"). Polymers in this group are prepared by the reaction of citric acid, cis-aconitic acid, α-ketoglutaric acid, succinic acid, fumaric acid, malic acid, and oxaloacetic acid with physiologically tolerable polyol compounds such as glycerol, glycerol esters, propylene glycol, mannitol, and sorbitol.

One application of these polymers is in surgical repair, especially bone repair. Compounds consisting of monomers having unsaturated vinyl groups which are in the form of a relatively low molecular weight viscous fluid can be compounded as a paste and used to form a moldable composition. The unsaturated vinyl groups can subsequently be cross-linked in a controlled manner through the action of a cross-linking agent to form a rigid composition, as is the practice in preparing bone cements.

Some of the aims of work to date on polymeric materials for surgical repair have been controlled biodegradability, flexibility of formulation for tailoring at the surgical site, and achievement of aesthetically acceptable results. The need for such materials is especially acute in the treatment of wounds in military situations. In these applications, there are not only the exacting surgical demands of wound treatment, but the special logistical demands of military utilization. Unfortunately, the state of development of surgical repair materials to date, while promising, has not yet been brought to a satisfactory level.

Conventional bone cement, polymethyl methacrylate (PMMA) is applied in the operating room by mixing powdered polymerized methylmethacrylate in combination with a small amount of benzoyl peroxide and liquid methylmethacrylate monomer. Since the monomer is a reactive molecule and tends to polymerize with itself slowly over time, hydroquinone is added to inhibit spontaneous free radical polymerization. Dimethyl toluidine (DMT) is also included to reduce the threshold temperature for the formation of free radicals by the benzoyl peroxide. When the liquid and powder are mixed by the surgeon, the PMMA powder is partially dissolved by the solvent action of the MMA monomer to form an opaque, viscous liquid. The mixture forms a rock-hard substance within about 10 minutes as a result of free radical polymerization. The original prepolymerized PMMA powder is chemically and mechanically bonded with the surrounding newly formed PMMA.

PMMA is not biodegradable. A biodegradable polymer having controlled biodegradability; significant adherence to the site (either tissue or bone); moldability within an acceptable working time; adequate physical strength; environmental stability; and ability to incorporate sustained release drugs, hormones, growth factors, and other biologically active compounds would be preferable for use as an alternative bone cement and polymer for controlled release.

A particularly promising material is poly(propylene glycol fumarate)(PPF). This is a biocompatible, biodegradable polymer synthesized from one of the Krebs cycle compounds which can be formulated in a molecular weight range well-suited for preparing pastes or moldable putties. In addition, certain members of this class of polymers are unsaturated and therefore potentially cross-linkable. Under proper control, this cross-linking characteristic may be exploited to convert a deformable mass to a rigid structure having good physical properties that is still biodegradable.

Poly(propylene glycol fumarate) is formed by reacting fumaric acid, $[C_2H_2(COOH)_2]$, is four-carbon molecule found in all cells of the body, and propylene glycol, $[CH_2(OH)CH_2(OH)CH_3]$, a three-carbon molecule with physical and chemical properties similar to glycerin. When propylene glycol, a viscous liquid, and fumaric acid, a white powder, are mixed together and heated, the carboxyl group on one end of the fumaric acid reacts with the hydroxyl group on one end of the propylene glycol. A water molecule is released and the fumaric acid and propylene glycol molecules covalently bond together via an ester to form a dimer. Because the dimer has both a free carboxyl group and a free hydroxyl group, additional fumaric acid molecules or propylene glycol molecules can react with the dimer to form a trimer, which can react to form a tetramer, then a pentamer, etc.

Poly(propylene glycol fumarate) (PPF) has completely different properties from either propylene glycol (PG) or fumaric acid (FA). Its physical properties depend upon the molecular weight of the polymer formed. With polymers of small molecular weight, only a few units in length the PPF is a clear, yellow liquid. As the polymer molecules increase in size, the PPF becomes more and more viscous until it is essentially a solid yellow plastic at room temperature. PPF is dissolved by most common organic solvents, including ethanol, ethyl acetate, chloroform, ether, and methylmethacrylate monomer.

The PPF prepolymer possesses two chemical properties that are critical for its functioning in a biodegradable bone cement. The first is its ease of degradation. The second is that each submit contains a carbon-carbon double bond, contributed by the fumaric acid, representing a potential site for further polymerization via free radical polymerization.

Methods for preparing PPF that have been reported include suspension polymerization in silicone oil and bulk polymerization. As described by Donald L. Wise, et al., in *Biopolymeric Controlled Release Systems*, Vol. II, Chapter 11, pages 170–184 (1986), in suspension polymerization, the polymer appears to form first in the oil phase due to the solubility of diethyl fumarate in silicone oil. As the forming polyester reaches higher molecular weight, solubility in the glycol phase becomes favored and the site of polymer growth moves to the glycol. Polymerization is initiated at atmospheric pressure at a temperature of 180° C. An acid catalyst such as p-toluene sulfuric acid is used. Following about 90 hr at these conditions, the reactant mixture is refluxed under 20 mm Hg vacuum until desired molecular weight is reached.

In the bulk polymerization process, the reactants are heated at about 140° C. The distillate collected in this procedure is largely ethanol containing some diethyl fumarate. If a solid product is desired, the reaction is carried out at higher temperatures, up to 220° C., using a distillation column. Final stripping is accomplished by application of vacuum.

In either procedure, the molecular weight of the product is determined by the amount of time at elevated temperatures. When high molecular weight material is desired, the polymerization is permitted to proceed to a point where the product is a solid at room temperature, melting about 80° C. Work has been done both with fluid, low molecular weight polymer, and with high molecular weight polymer dissolved in solvent. This liquid is converted to a paste or putty form through addition of a powdered filler material such as calcium carbonate or tricalcium phosphate to form a bone cement. The other component of the bone cement mixture is a crosslinking agent for converting the plastic material applied to the wound to a solid form. Chemical crosslinking between the polyester molecules forming the fluid component of the formulation is initiated by addition to the mixture of a free radical generator, such as a peroxide. Only a modest degree of cross-linking is desired, just sufficient to convert the mixture from a plastic mass to a solid. The crosslinking must not be so extensive and thorough that the resulting solid becomes nonbiodegradable.

As described in *Biopolymeric Controlled Release Systems* Volume II, Donald L. Wise, et al., Chapter 11, 170–184, and "Synthesis and Properties of Polymers for Biodegradable Implants", and by A. C. Ibay, et al., 505–509, a variety of poly(propylene glycol fumarate) compositions have been prepared and characterized for use in vivo as bone cements and biodegradable implants. However, as described by both Ibay, et al., at page 506, and Wise, et al., none of these polymer preparations had the desired molecular weight and physical characteristics for use as a bone cement, each having problems with cross-linking and mechanical strength, being either too hard and brittle, too soft, or rubbery. These problems are aggravated by the failure of the described methods to maintain the starting ratio of PG:FA due to evaporation of the PG during heating at temperatures in excess of about 140° C.

It is therefore an object of the present invention to provide biodegradable, biocompatible polymeric materials having mechanical and chemical properties suitable for biochemical use as bone cements and tissue implants.

It is another object of the invention to provide methods for polymerizing poly(propylene glycol fumarate) in a wide range of molecular weights for use in biomedical applications.

It is a further object of the invention to provide methods for polymerizing poly(propylene glycol fumarate) having a controlled range of cross-linking and degradability.

It is still further object of the present invention to provide a poly(propylene glycol fumarate) composition having a narrow, controlled range of molecular weight with a controlled ratio of end groups.

SUMMARY OF THE INVENTION

The present invention includes highly reproducible poly(propylene glycol fumarate) compositions having a controlled end group ratio and range of molecular weights with minimal low molecular weight and excessively high molecular weight fractions, and methods for their manufacture. Compositions having a preferred weight average molecular weight (Mw) of between about 500 and 3000 and a number average molecular weight (Mn) of between about 300 and 2000 are especially useful in biomedical applications as bone cements and tissue implants or glues.

The method of the present invention yields a polymer having a specific molecular weight range and composition, in contrast to the prior art. There are three embodiments of the method for polymerizing propylene glycol (PG) and fumaric acid (FA): melt polymerization of non-volatile starting materials; step polymerization of the polymer by the addition of two units to the polymer ends at each step; and reaction of the materials under conditions maintained so that only the condensation byproduct, water, is removed during the reaction. The later is achieved by either reacting PG with FA in two steps, first at a temperature of between about 100° C. and 130° C. in a closed system with a trap to collect the water so minimal PG is evaporated out and second at a temperature of 180° C. for 1 to 3 hours, or by reacting PG with FA in the pressure of a solvent which removes water exclusively as an azeotrope.

Various embodiments of the PPF polymers include polymers incorporating lactic acid groups into the polymer for increased sensitivity to hydrolysis and polymers formed from maleic acid, maleic anhydride, citraconic acid or citraconic anhydride, in place of or in combination with fumaric acid.

DETAILED DESCRIPTION OF THE INVENTION

The present invention is a method for the synthesis of poly(propylene glycol fumarate) (PPF) polymeric compositions, and variations thereof, for use in biodegradable, biomedical compositions including bone cement composites (BBCC), polymeric matrices for controlled release drug delivery applications, and tissue adhesives.

The following factors have been discovered to have a direct effect on the properties of the polymer with regard to mechanical strength, consistency (solid or paste), degradability, and crosslinking.

1. Polymer molecular weight. Bone cement applications require a weight average molecular weight (Mw) in the range of 600 to 3000. Polymers with higher molecular weights cannot be applied as putty paste. Small changes in the molecular weight have a dramatic effect on the mechanical strength, degradation rate and crosslinking properties.

2. Distribution of the polymer molecular weight (polydispersity). Increasing the amount of low Mw fraction relative to high Mw fraction dramatically decreases the mechanical strength.

3. Polymer end groups. Two types of end groups exist: carboxylic acid end groups, when fumaric acid is the terminal group, and hydroxyl end groups, when propylene glycol is the terminal group. Carboxylic acid groups (—COOH) are very hydrophilic, form strong hydrogen bonds, have high cohesion energy (adhesiveness) and can be crosslinked with divalent ions (e.g., $Ca^{2+}$) by salt formation. This is very important when $Ca^{2+}$ is present in the bone cement mixture. Hydroxyl groups are less hydrophilic, less reactive, less sticky, and do not form salts under aqueous conditions. The polymer's properties depends upon the balance between these end groups.

As discussed in the background of the invention, Ibay, et al., studied a poly(propylene fumarate) polymer for its appropriateness as a bioerodible bone cement matrix. Table 1a shows the methods and conditions, while Table 1b summarizes the reactions. After the polymer was synthesized and characterized, crosslinking was attempted using 5% N-vinyl-2-pyrrolidone and benzoyl peroxide.

TABLE 1a

Summary of Polycondensation Methods

| Method | Fumarate Derivative | Solvent | Temperature | Time | Catalyst |
|---|---|---|---|---|---|
| Transesterification (Eq. 1) | Diethyl Fumarate | Bulk | 200° C. | 24 h | PTSA[d] |
| Acid Chloride (Eq. 2) | Fumaryl Chloride | Bulk | 0° C. | 24 h | None |
| Acid Chloride-Semiester (Eq. 3) | Fumaryl-Chloride-mono-ethyl-ester[a,c] | Bulk | 0°, then 200° C. | 24 h | None |
| Carbodiimide (Eq. 4) Dicarbodiimide[b,c] | Fumarate | THF | 67° C. | 24 h | None |
| Esterification (Eq. 5) | Fumaric Acid | Propylene Glycol | 200° C. | 24 h | None |

[a]Synthesized by treating fumaric acid-mono-ethyl ester with thionyl chloride.
[b]Generated in situ from fumaric acid and dicyclohexyl carbodiimide.
[c]Comonomer-feed technique used.
[d]Para-toluene sulfonic acid.

TABLE 1b

Summary of Reactions

1. $\text{EtO}-\overset{\overset{\text{O}}{\|}}{\text{C}}-\text{CH}=\text{CH}-\overset{\overset{\text{O}}{\|}}{\text{C}}-\text{OEt} + \text{HOCH}\overset{\overset{\text{CH}_3}{|}}{}\text{CH}_2\text{OH} \xrightarrow{\text{PTSA}} \text{EtO}-\left[\overset{\overset{\text{O}}{\|}}{\text{C}}-\text{CH}=\text{CH}-\overset{\overset{\text{O}}{\|}}{\text{C}}-\text{OCH}_2\overset{\overset{\text{CH}_3}{|}}{\text{CH}}\text{O}\right]_n-\text{H}$ $\underline{1}$ 2. $\text{Cl}-\overset{\overset{\text{O}}{\|}}{\text{C}}-\text{CH}=\text{CH}-\overset{\overset{\text{O}}{\|}}{\text{C}}-\text{Cl} + \text{HOCH}_2\overset{\overset{\text{CH}_3}{|}}{\text{CH}}\text{OH} \longrightarrow \text{HOCH}_2\overset{\overset{\text{CH}_3}{|}}{\text{CH}}\text{O}-\left[\overset{\overset{\text{O}}{\|}}{\text{C}}-\text{CH}=\text{CH}-\overset{\overset{\text{O}}{\|}}{\text{C}}-\text{OCH}_2\overset{\overset{\text{CH}_3}{|}}{\text{CH}}\text{O}\right]_n-\text{H} + \text{HCl}$ $\underline{2}$ 3. $\text{HO}-\overset{\overset{\text{O}}{\|}}{\text{C}}-\text{CH}=\text{CH}-\overset{\overset{\text{O}}{\|}}{\text{C}}-\text{OEt} \xrightarrow{\text{SOCl}_2} \text{Cl}-\overset{\overset{\text{O}}{\|}}{\text{C}}-\text{CH}=\text{CH}-\overset{\overset{\text{O}}{\|}}{\text{C}}-\text{OEt} \xrightarrow[-\text{HCl}]{\text{HOCH}_2\overset{\overset{\text{CH}_3}{|}}{\text{CH}}\text{OH}}$ $\text{HO}-\overset{\overset{\text{CH}_3}{|}}{\text{CH}}\text{CH}_2\text{O}-\overset{\overset{\text{O}}{\|}}{\text{C}}-\text{CH}=\text{CH}-\overset{\overset{\text{O}}{\|}}{\text{C}}-\text{OEt} \xrightarrow{\Delta} \underline{1}$ 4. $\text{HO}-\overset{\overset{\text{O}}{\|}}{\text{C}}-\text{CH}=\text{CH}-\overset{\overset{\text{O}}{\|}}{\text{C}}-\text{OH} \xrightarrow{\text{DCC}} \text{RNH}-\overset{\overset{\text{RN}}{|}}{\text{C}}-\text{O}-\overset{\overset{\text{O}}{\|}}{\text{C}}-\text{CH}=\text{CH}-\overset{\overset{\text{O}}{\|}}{\text{C}}-\text{O}-\overset{\overset{\text{NR}}{|}}{\text{C}}-\text{NHR} \xrightarrow{\text{HOCH}_2\overset{\overset{\text{CH}_3}{|}}{\text{CH}}\text{OH}}$ $\underline{2} + \text{RNH}-\overset{\overset{\text{O}}{\|}}{\text{C}}-\text{NHR}$ 5. $\text{HO}-\overset{\overset{\text{O}}{\|}}{\text{C}}-\text{CH}=\text{CH}-\overset{\overset{\text{O}}{\|}}{\text{C}}-\text{OH} + \text{HOCH}_2\overset{\overset{\text{CH}_3}{|}}{\text{CH}}-\text{OH} \xrightarrow{-\text{H}_2\text{O}}$

TABLE 1b-continued
Summary of Reactions $$HO-\underset{CH_3}{\underset{|}{CHCH_2}}-O-\underset{O}{\underset{\|}{C}}-CH=CH-\underset{O}{\underset{\|}{C}}-O-CH_2\underset{CH_3}{\underset{|}{CH}}-OH \xrightarrow{-HOCH_2\underset{CH_3}{\underset{|}{CHOH}}} \underset{\Delta}{} \underline{2}$$

DCC = ⟨cyclohexyl⟩—N=C=N—⟨cyclohexyl⟩

R = —⟨cyclohexyl⟩

It was found that the esterification reaction yielded a high molecular weight material with a number average molecular weight (Mn) of $6 \times 10^6$. A lower molecular weight fraction (Mn equal to 3,600) was also produced by the same esterification method. After crosslinking the fractions, Ibay et al concluded that the resultant polymeric systems were not fully suited to their desired application. The higher molecular weight polymer became hard too quickly, while the lower molecular weight polymer took longer, requiring heating to harden. It was suggested that a poly(propylene fumarate) with Mn somewhere between 3,600 and $6 \times 10^6$ was necessary for bioerodible cement applications.

In other studies, PPF was prepared by a melt condensation in which fumaric acid was reacted heterogeneously with propylene glycol at a temperature greater than 140° C. Water is removed during the reaction to form the polymer.

It is necessary to maintain a constant ratio between the propylene glycol and fumaric acid throughout the reaction to yield a polymer with controlled molecular weight, end group ratio and polydispersity. The ratio between fumaric acid and polypropylene glycol is hard to control in melt polycondensation using a heterogeneous mixture due to the evaporation of the propylene glycol (boiling point 187° C.) during the reaction, even though excess propylene glycol (10%) is generally added. As a result, the end products include low molecular weight molecules including propylene glycol, fumaric acid, and fumaric acid-propylene glycol dimers in varying quantities.

In one embodiment, the present invention eliminates the problem of propylene glycol-fumaric acid dimer production during melt condensation by using non-volatile oligomers of propylene glycol and fumarate as starting materials. This maintains the stochiometric ratio during polymerization to yield the desired polymer free of propylene glycol and its dimers.

Melt Condensation of poly(propylene glycol fumarate):
Using Non-Volatile Starting Materials
The non-volatile starting materials are:
1. bis-propylene glycol fumarate (PFP trimer) and longer oligomers thereof.
2. 1,2 propylene glycol dibutenoate (BPB trimer) and longer oligomers thereof.
3. Propylene glycol oligomers or short polymers (e.g., polypropylene or ethylene glycols) having a molecular weight range between 100 and 5,000.

The PPF polymers are synthesized by:
1. PFP trimer or other oligomer with hydroxyl end groups is reacted with fumaric acid or diethyl fumarate.
2. Oligomers with hydroxyl end groups are reacted with oligomers having carboxylic acid end groups, for example, PFP trimer and BPB (MPM) trimer.
3. Non-volatile propylene or ethylene glycol oligomers or polymers having a Mw range between 100 and 5,000 are reacted with fumaric acid or oligomers with carboxylic acid end groups, for example, PFP trimer or heptamer.

The molecular weight, polydisperity, and end groups are controlled by the ratio between the reactants and the reaction time and temperature.

In another embodiment, the present invention eliminates the problem of maintaining a stoichiometric ratio of propylene glycol to fumaric acid by alternately adding bis-propylene glycol fumarate (PFP) trimer or 1,2 propylene glycol dibutenoate (BPB) trimer so that the polymer increases by two units at each step.

Step Polymerization of poly(propylene glycol fumarate).
1. bis-propylene glycol fumarate (PFP) trimer is prepared by reacting fumaric acid and propylene oxide using the method of Wygant, et al., U.S. Pat. No. 3,360,546 issued Dec. 26, 1967, generally describing the preparation of hydroxyalkyl fumerate esters.

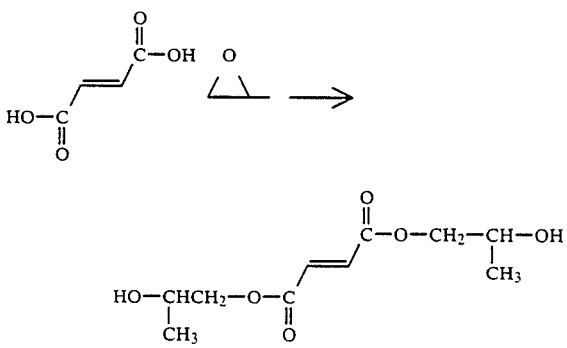

2. 1,2 propylene glycol dibutenoate (BPB) trimer is prepared by reacting propylene glycol and maleic anhydride:

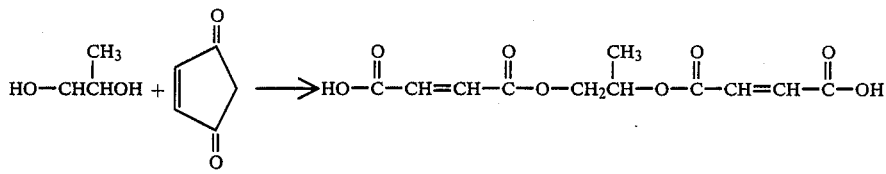

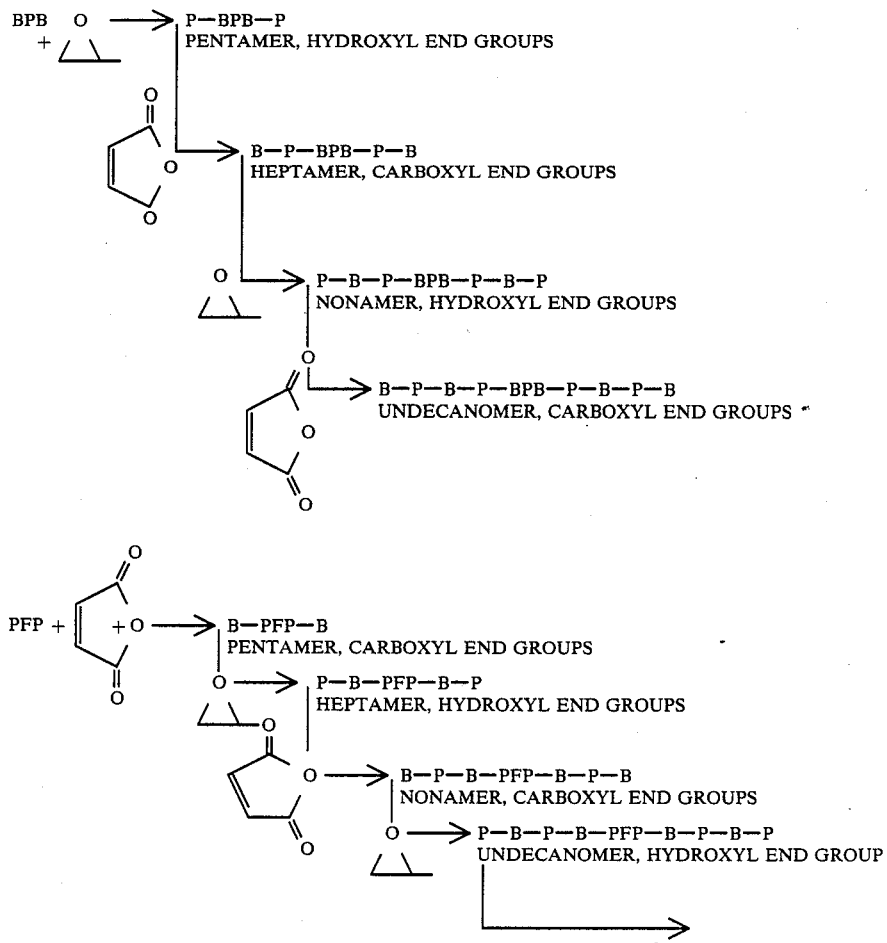

Step polymerization is carried out using PFP or BPB (MPM) trimers as starting materials to form pentamers, heptamers, etc., by alternating the same reactions used for the formation of the PFP and BPB trimers.

In another embodiment, the present invention eliminates the problem of maintaining a stoichiometric ratio of propylene glycol to fumaric acid by either reacting fumaric acid and propylene glycol in two steps or adding to a reaction mixture consisting of PG and FA a solvent that forms an azeotrope with water.

Controlled Two-Step Condensation, Evaporation Synthesis.

Fumaric acid and propylene glycol are reacted reproducibly under specific conditions using either of two approaches:

(a) Reacting fumaric acid and propylene glycol in two steps: first, heating at a temperature where propylene glycol is not removed by evaporation, between about 100° C. and 130° C., for 10 to 20 hours, until a clear mixture is obtained; secondly, heating the mixture at 180° C. for about 1 to 2 hours to yield the desired polymer.

(b) Adding to a reaction mixture consisting of PG and FA a solvent that forms an azeotrope with water. Xylene is the preferred solvent since its boiling point is around 140° C.

Variations of PG:FA Polymers

Unsaturated polymers having different properties, including greater flexibility, can be prepared by substituting maleic acid, maleic anhydride, citraconic acid or citraconic anhydride for fumaric acid. These materials have chemical structures similar to fumaric acid and are nontoxic, but, unlike fumaric acid which melts at 300° C., the melting points of these molecules are less than 140° C. (maleic acid 134° C., citraconic acid 95° C., with the anhydrides having lower melting points than the acids). As a result, these compounds react homogeneously with propylene glycol at a temperature greater than 140° C.

Polymers can also be prepared which overcome one of the disadvantages of prior art PPF bone cements, their slow biodegradability. Most of the prior art PPF material is removed by phagocytosis accompanied by very slow hydrolysis. The rate of hydrolysis must be increased for the polymer to be used as a vehicle for controlled drug delivery. This is accomplished by incorporating into the polymer a comonomer which provides more labile bonds. For example, copolymerization with lactic acid (LA) or glycolic acid (GA) yields a polymer containing lactic acid linkages which are more readily hydrolyzable than the bonds in PPF. MPM-PFP trimers (1:1) are reacted with various amounts of lactide or glycolide with or without catalyst.

The amount of LA or GA in the copolymer can be varied from 0 to 95%. However, increasing LA decreases the number of double bonds in the polymer available for crosslinking. While crosslinking is very important for bone cements, it is less so for drug delivery.

The following methods are useful in the characterization of polymers according to the present invention, as described in the subsequent non-limiting examples.

Polymers were analyzed for carboxyl groups by titration of a acetonic solution with 0.1N NaOH to the end point of phenol red. Typically, 0.5 g of polymer is dissolved in 10 ml acetone. To this solution is added three drops of standard phenol red solution, and the solution titrated.

Elemental analyses were performed by Glabraith Laboratories, Knoxville, TN. Melting points were recorded on a Fisher-Johns melting point apparatus. IR Spectroscopy was performed on a Perkin-Elmer Series 1420 dispersive spectrophotometer.

The molecular weight of polymers was determined relative to polystyrene standards in chloroform solutions (10 mg/ml) by Gel Permeation Chromatography (GPC) on a Perkin-Elmer instrument equipped with a LKB-2140 diode array multiple-wavelength UV detector. Two Perkin-Elmer PL-gel (10 μm) columns (exclusion limits: 300–1,500,000), connected in series, were used. The flow rate was 1.5 ml/min.

Vapor pressure osmometry (VPO) measurements were performed in a Knauer osmometer type 11.00 (Knauer, West Germany) equipped with a digital meter type 06.00. Samples in chloroform (15 mg/g) were measured in chloroform at 45° C. For the molecular weight determination, a calibration curve was prepared using polyethylene glycol standards (Polysciences) of molecular weight range 210 and 10,000. Mechanical strength was determined in an INSTRON 1331 materaisl test system using ASTM standard F451-76 PPF cylindrical specimens (6×12 mm) composed of 28% PPF, 5% methylmethacrylate (MMA), 33% tricalcium phosphate and 33% calcium phosphate crosslinked with 1% benzoylperoxide and 0.2% dimethyl toloidine.

EXAMPLE 1

Synthesis of polypropylene glycol fumarate (PPF) using non volatile glycols

A. Synthesis of PPF from PFP trimer or BPB (MPM) trimer and FA.

Bis-propylene glycol fumarate (PFP trimer) and propylene glycol dibutenoic ester, BPB (MPM) trimer, were prepared by the reaction of fumaric acid and propylene oxide (PFP) and the reaction of propylene glycol and maleic anhydride (MPM), respectively. These trimers were used to synthesize PPF polymer by melt polymerization or step polymerization.

Preparation of PFP trimer.

In a 1000 ml three neck round bottom flask equipped with an overhead mechanical stirrer (vacuum sealed) and condenser with drying tube, 1 mole fumaric acid (116 g) is dissolved in 150 ml 4-methyl 2-pentanone. The flask is placed in a heating mantle. At reflux, three ml pyridine is added as a catalyst. Propylene oxide is slowly added dropwise from a dripping funnel. Excess propylene oxide is used (150 ml). At six hours another 150 ml portion of propylene oxide is added dropwise. The reaction continues for twenty hours, until the reaction mixture is a clear yellow liquid, totally devoid of solid fumaric acid. Immediately thereafter, 300 ml 10% $Na_2 HPO_4$ solution is added. The mixture is placed in a 1000 ml separatory funnel and vigorously shaken. The mixture is then set aside until there is a distinct separation of the phases. The lower water phase is discarded while the upper phase, which contains the product, is washed twice with 500 ml 5% KCL solution. The phases are again allowed to separate. The lower phase is discarded while the upper phase is filtered over magnesium sulfate. The product is then placed in a tared 1000 ml round bottom flask and rotary evaporated until all solvents have been removed. The resulting product is then lyophilized to remove trace quantities of solvents.

Preparation of MPM Trimer

One mole maleic anhydride (98 g) is dissolved in 100 ml toluene in a 500 ml three neck round bottom flask equipped with a condenser. The flask is submersed in a 100° C. oilbath. 0.5 mole propylene glycol (39 g) is slowly dripped into this sealed system. The reaction is stirred for the duration of the reaction, about 24 hours. After the appropriate time, the reaction vessel is removed from the oilbath. The reaction mixture is transferred to a 1000 ml separatory funnel and allowed to settle until two distinct phases are observed. The lower phase contains the product dissolved in ether. The upper toluene phase is discarded. Hexane is added to the ether reaction mixture and the phases again allowed to settle. The lower phase, containing the product, is then transferred to a tared round bottom flask and rotary evaporated until all excess solvent is removed. The product is then lyophilized to remove trace quantities of solvents.

Reaction between PFP trimer and Fumaric Acid (1:0.65).

In a large test tube equipped with a small magnetic stirbar, 3.25 g fumaric acid is added to 10 g PFP trimer. The tube is placed in a 100° C. oilbath, and stirred vigorously. Every 20 minutes, water produced in the reaction is removed by wiping the inside of the tube with a Kimwipe. Samples are taken through a long Pasteur Pipette. After 2 hours, the tubes are removed from the oilbath. Reactions of PFP trimer and fumaric acid at different ratios are performed similarly.

Table 2 describes the reaction between PFP and various amounts of fumaric acid.

TABLE 2

| Ratio | Molecular Weight | | Acid Content | % Unreacted | Mech. |
|---|---|---|---|---|---|
| (PFP:FA) | (Mw) | (Mn) | (mmol COOH/G) | fumaric acid | Strength |
| 1:0.50 | 1152 | 589 | 0.81 | 0 | 8.5 |
| 1:0.65 | 1166 | 590 | 1.06 | 0.5 | 9.5 |
| 1:0.70 | 1102 | 592 | 1.20 | 1.0 | 11.0 |
| 1:0.75 | 1155 | 578 | 1.27 | 1.5 | 11.5 |

[a]Reaction at 180° C. under atmospheric pressure for 2 hours.

The acid content and the relative percentage of unreacted fumaric acid increase with increasing amount of fumaric acid relative to trimer. The mechanical strength also increases with the increase in acid content, suggesting that acid end groups in the polymer influence the mechanical strength, probably due to the increase in hydrogen bonding of the acid groups. The PFP:FA polymer having a ratio of (PFP:FA)(1:0.65) has the minimum unreacted acid in combination with high mechanical strength.

The distribution of the molecular weights of the polymers is similar. The PFP:FA polymer is built of four equal fractions. For the PPF produced from PFP:FA (1:0.5), the molecular weight fractions (Mw/Mn) were 28%: 1964/1616, 29%: 896/884, 26%: 569/550, and 16%: 244/215.

The reaction rate of the polymerization of PPF is described in Tables 3 and 4.

TABLE 3

Time Dependence and Reproducibility of the Reaction of PPF trimer and fumaric acid[a,b]

| time (h) | molecular weight | | % unreacted fumaric acid | acid content mmol (COOH/g) | mech. stren. (MPa) |
|---|---|---|---|---|---|
| | (Mw) | (Mn) | | | |
| A. Reaction of PFP trimer and fumaric acid, 1:1 ratio | | | | | |
| 1 | 387 | 202 | 11.7 | 1.09 | 5.3 |
| | 332 | 176 | 12.3 | 1.09 | 4.6 |
| 1.5 | 488 | 259 | 5.0 | 1.01 | 6.2 |
| | 487 | 242 | 4.8 | .98 | 4.8 |
| 2 | 633 | 266 | 1.3 | 0.93 | 9.8 |
| | 683 | 306 | 1.1 | 1.09 | 10.7 |
| B. Reaction of PFP trimer and fumaric acid, 1:0.5 ratio | | | | | |
| 1 | 354 | 176 | 6.9 | 0.97 | 3.5 |
| | 404 | 233 | 8.9 | 0.88 | 4.1 |
| 1.5 | 513 | 251 | 1.4 | 0.87 | 3.9 |
| | 628 | 275 | 0.5 | 0.74 | 4.8 |
| 2 | 634 | 315 | 0.0 | 0.90 | 6.7 |
| | 973 | 357 | 0.1 | 0.85 | 6.8 |

[a]reaction at 180° C. under atmospheric pressure
[b]samples in duplicate

TABLE 4

Molecular weight as a function of the Reaction time between PFP trimer and fumaric acid

| time (min) | molecular weights | |
|---|---|---|
| | Mw | Mn |
| 60 | 418 | 204 |
| 90 | 492 | 221 |
| 120 | 874 | 253 |
| 150 | 728 | 330 |
| 180 | 810 | 340 |
| 210 | 867 | 396 |
| 240 | 978 | 403 |
| 270 | 1145 | 362 |
| 300 | 1218 | 458 |

The molecular weight of the polymer increases gradually between two and four hours. The Mw does not change, while Mn changes slightly, indicating that the reaction is not dramatically sensitive to the reaction time. This simplifies its preparation. The polymer formed after two hours is still liquid and can be used as a paste. It also demonstrates high mechanical strength, 15.5 MPa. The PPF reacted at a molar ratio of PFP trimer:fumaric acid of 1:0.65 for two hours at 180° C. shows excellent reproducibility in all parameters. Mechanical strengths ranges from 12.5 to 15 MPa.

B. Synthesis of PPF from MPM pentamer and FA, Fumaric diacid, or MPM trimer

Another non-volatile dialcohol useful for the controlled synthesis of PPF is MPM pentamer derived from MPM trimer after reaction with propylene oxide. The pentamer is reacted with a diacid, fumaric acid, or with MPM trimer. Table 5 demonstrates the results of the reaction of MPM pentamer and fumaric acid (1:0.65) as a function of time.

Reaction between MPM Pentamer and Fumaric Acid (1:0.65).

The reaction is performed identically to that of the PFP trimer and fumaric acid with the exception that 2 g fumaric acid are added to 10 g MPM pentamer. Again, the proper stoichiometric quantities of starting materials are used for reactions of starting materials at different ratios.

TABLE 5

Reproducibility of Molecular weight and Acid Content of MPM Pentamer-fumaric acid polymerizations[a,b]

| reaction time (min) | mol. weight Mw/Mn | Acid COOH/g | mech. strength |
|---|---|---|---|
| 30 | 614/293 | 1.55 | 4.6 |
| | 580/257 | 1.62 | |
| | 634/264 | 1.58 | |
| 60 | 918/379 | 1.48 | 8.9 |
| | 1040/390 | 1.53 | |
| | 1039/388 | 1.51 | |
| 90 | 1276/474 | 1.43 | 16.04 |
| | 1280/460 | 1.38 | |
| | 1319/491 | 1.22 | |
| 105 | 1602/563 | 1.23 | 15.93 |
| | 1503/474 | 1.25 | |
| | 1650/510 | 1.18 | |
| 120 | 2139/666[c] | 0.96 | — |
| | 2512/476 | 0.87 | |
| | 2360/490 | 0.84 | |

[a]reaction of MPM pentamer and fumaric acid at a molar ratio of 1:0.65 at 180° C. at atmospheric pressure
[b]each reaction step was performed in triplicate
[c]too viscous to apply The molecular weight is constant after one hour of reaction. The Mn derived by this reaction is higher than that of the reaction using PFP trimer, as is expected from using a higher molecular weight starting material (pentamer Mw 388, trimer Mw 232).

C. Synthesis of PPF trimer and diethyl fumarate

PPF was prepared by reacting PFP trimer with diethyl fumarate.

PFP trimer:diethyl fumarate (1:0.7) was reacted in a round bottom flask equipped with a magnetic stirbar at 180° C. at atmospheric pressure. After two hours, the material had a molecular weight (Mw/Mn) of 637/341; after four hours, 2005/256; and after six hours, 2526/297.

Although this polymerization yields a fairly high molecular weight material, the polymer is of the consistency of a gel not suitable for biomedical purposes.

D. Synthesis of PPF from PFP and MPM trimers

PPF was prepared from the reaction between PFP and MPM trimers. This reaction is homogeneous since both trimers are miscible in each other. Reactions were conducted at 180° C. Table 6 demonstrates the relatively high reproducibility of the reaction of PFP trimers:MPM trimers (1:1) for 2 hours at 180° C.

Reaction between MPM trimer and PFP trimer (1:1).

These reactions are also similar to those of the PFP trimer and fumaric acid reactions. However, the reaction is homogeneous rather than heterogeneous since both starting materials are liquid. For a ratio of 1:1, 5 g PFP trimer is reacted with 5.86 g MPM trimer. Quantities for the different ratios are varied accordingly.

TABLE 6

Molecular weight as a function of the time of Reaction between MPM and PFP trimers[a]

| sample | molecular weight (Mw/Mn) | | |
|---|---|---|---|
| | 60 min | 90 min | 120 min |
| A[b] | 1193/424 | 1200/496 | 1304/459 |
| B | 1012/424 | 1350/508 | 1398/505 |
| C | 967/407 | 1305/479 | 1354/509 |
| D | 1216/535 | 1411/581 | 1457/532 |
| E | 1035/457 | 1213/497 | 1300/521 |

[a]reaction of MPM and PFP trimers at a ratio of 1:1 at atmospheric pressure at 180° C.
[b]acid content for sample A: 60 min, 1.46; 90 min, 1.51; and 120 min, 1.43 mmol COOH/g.

The molecular weight remains the same after 60 minutes. The polymers remain as liquids for use in paste form. The mechanical strength and acid content are similar for polymers reacted for between 50 and 120 minutes (11.4–13.4 MPa). As expected, the polymers with a higher ratio of MPM to PFP had a greater acid content. In general, polymers with greater MPM starting ratios yielded high molecular weight polymers. The effect of the ratio between the prepolymers is shown in Table 7.

TABLE 7

Molecular Weight, Acid Content, and Mechanical Strength as a function of the reaction of MPM and PFP trimers at various molar ratios[a].

| ratio MPM/PFP | molecular weight | | acid content | mech. stren. |
|---|---|---|---|---|
| | Mw | Mn | mmol COOH/g | MPa |
| 1:1[b] | 1015 | 438 | 1.74 | 13.5 |
| | 1419 | 466 | 1.89 | 14.8 |
| 1:0.5[b] | 1055 | 441 | 2.08 | 12.6 |
| | 1444 | 516 | 1.94 | 13.4 |
| 0.5:1[b] | 671 | 287 | 1.37 | 8.5 |
| | 700 | 261 | 1.39 | 7.6 |
| 1:0.7 | 1386 | 493 | 1.49 | 15.6 |
| 0.7:1 | 738 | 283 | 1.55 | 11.8 |

[a]reaction conducted at 180° C. for 90 min at amos. pressure
[b]samples run in duplicate When the reaction was conducted at a lower temperature (140° C.), a low molecular weight polymer with poor mechanical strength was obtained, as shown in Table 8.

TABLE 8

Reaction of MPM and PFP trimers at 140° C.

| ratio of MPM:PFP trimers | molecular weight | | acid content | mech. stren. |
|---|---|---|---|---|
| | (Mw) | (Mn) | (mmol COOH/g) | MPa |
| 1:1 | 311 | 196 | 3.05 | 2.80 |
| 1:0.7 | 312 | 171 | 3.20 | 2.15 |
| 0.7:1 | 721 | 182 | 3.35 | 2.02 |

F. Synthesis of PPF from higher molecular weight oligomers

A higher molecular weight PPF with minimal low molecular weight fractions can be synthesized from non-volatile starting materials, using higher molecular weight oligomers made by step polymerization. PFP trimer was reacted with PFP pentamer in varying ratios, and a time dependence study was performed. The results are shown in Tables 9 and 10.

Reaction between PFP trimer and PFP pentamer (1:1).

Again, the procedure for this set reactions is similar to that of the MPM trimer and PFP trimer reactions and is also homogeneous. In the large tube equipped with a small magnetic stirbar, 5 g PFP trimer is added to 9.2 g PFP pentamer. The tube is submersed in a 180° C. oil-bath and the reaction mixture allowed to stir for 2 hours, or the given reaction time. The inside of the tube is wiped dry with a Kimwipe to remove excess water. Reactions of materials at different stoichiometric ratios are performed similarly.

Reaction between MPM trimer and MPM pentamer (1:1).

As described above, 2.5 g MPM trimer are reacted with 3.6 g MPM pentamer.

Reaction between PFP heptamer and PFP nonamer (0.75:1).

As described before, 2 g PFP heptamer is reacted with 3.19 g PFP nonamer.

TABLE 9

Reaction of PFP trimer and PFP pentamer[a]

| molar ratio trimer/pent | molecular weight (Mw/Mn) | | | acid content mmol COOH/g | mech. stren. MPa |
|---|---|---|---|---|---|
| | 60 min | 75 min | 90 min | | |
| (0.88:1) | 792/340 | 1070/449 | 1517/492 | 2.00 | 16.7 |
| | 860/379 | 1140/483 | 1407/569 | 1.86 | 14.3 |
| (1:0.75) | 737/371 | 1066/419 | 1222/479 | 1.95 | 13.4 |
| | 771/342 | 1083/401 | 1167/475 | 1.82 | 14.7 |
| (0.75:1) | 734/324 | 988/396 | 1110/469 | 1.71 | 12.7 |
| | 565/285 | 836/365 | 873/379 | 1.87 | 13.2 |

[a]reaction conducted at 180° C. under atmospheric pressure

TABLE 10

Reaction of PFP trimer and PFP pentamer: Time dependence[a]

| time (min) | molecular weight (Mw/Mn) |
|---|---|
| 60 | 552/286 |
| 75 | 663/324 |
| 90 | 651/322 |
| 105 | 750/349 |
| 120 | 966/369 |

[a]reaction of PFP trimer and PFP pentamer at a ratio of 1:1 conducted at 180° C. at atmospheric pressure.

The polymers made with a greater molar ratio of carboxyl end group starting material have a higher acid content. Additionally, in general, the greater the molar ratio of pentamer to trimer, the greater the molecular weight of the resulting polymer. The time dependence study demonstrates that polymer elongation is fairly constant over time.

A similar study was performed using MPM trimer and MPM pentamer as starting materials. The results are shown in Tables 11 and 12.

TABLE 11

Reaction between MPM trimer and MPM pentamer[a]

| molar ratio trimer/pent | molecular weight Mw/Mn | acid content mmol COOH/g | mech. stren. MPa |
|---|---|---|---|
| 0.88:1 | 1066/427 | 1.81 | 14.7 |
| 1:0.75 | 1067/418 | 2.13 | 15.6 |
| 0.75:1 | 1053/419 | 1.70 | 13.3 |

[a] reaction conducted at 180° C. for 1 hour under atmospheric pressure

TABLE 12

Reaction between MPM trimer and MPM pentamer: Time Dependence[a]

| time (min) | molecular weight (Mw/Mn) |
|---|---|
| 60 | 779/365 |
| 75 | 913/385 |
| 90 | 965/382 |
| 105 | 1225/500 |
| 120 | 1756/529 |

[a] reaction of PFP trimer and PFP pentamer at a ratio of 1:1 conducted at 180° C. at atmospheric pressure.

Again, the acid content of the resulting polymer is greatest when the relative amount of carboxylic end group starting material is high. Also, a drastic increase in molecular weight is observed between 90° and 105° minutes into the reaction. Varying the ratios of starting materials does not significantly change the molecular weights of the resulting polymers.

PPF has also been synthesized from larger molecular weight non-volatile oligomers: MPM pentamer was reacted with PFP pentamer in varying ratios and PFP monomer was reacted with both PFP trimer and PFP heptamer. The results are shown in Tables 13 and 14.

TABLE 13

Molecular Weight, Acid Content and Mechanical Strength as a function of the Reaction between MPM pentamer and PFP pentamer[a]

| molar ratio MPM/PFP | molecular weight (Mw/Mn) 15 min | 30 min | acid content mmol COOH/g | mech. stren. MPa |
|---|---|---|---|---|
| 1:1 | 527/307 | 771/373 | 1.98 | 14.2 |
| 1:0.75 | 497/289 | 650/321 | 1.89 | 12.5 |
| 0.75:1 | 558/303 | 813/360 | 2.51 | 16.2 |

[a] reactions conducted at 180° C. for 30 minutes under atmospheric pressure

TABLE 14

Molecular Weight, Acid Content and Mechanical Strength as a function of the Reaction between larger PFP oligomers[a]

| starting materials | molar ratio | molecular weight (Mw/Mn) | acid content mmol COOH/g | mech. stren. MPa |
|---|---|---|---|---|
| heptamer/nonamer | 0.85:1 | 1797/716 | 1.14 | 15.7 |
| trimer/nonamer | 1:1 | 1681/521 | 1.25 | 16.4 |

[a] reactions conducted at 180° C. under atmospheric pressure for 30 minutes

As shown before, increasing the ratio of carboxylic acid end group starting materials increases the acid content of the resulting polymer. Furthermore, the higher the molecular weight of the starting materials, the greater the molecular weight of the resultant polymer.

E. Synthesis of PPF from PEG or PPG

PPF was synthesized with high reproducibility using glycols longer than propylene glycol, low molecular weight poly(propylene glycol), PPG, or poly(ethylene glycol), PEG.

PPG and PEG polymers with molecular weights of 100 to 10,000 are commercially available (Aldrich Chemical Co, Inc., Milwaukee, WI; Polysciences, Inc, Warrington, PA). Since these polymers have a high boiling point (300° C.) they eliminate the problem of evaporation of the starting materials.

PEG (Mw 300 or 600) was reacted with fumaric acid or a dicarboxylic acid oligomer, e.g., MPM trimer and PFP pentamer. Polypropylene glycols, instead of propylene glycol, were also reacted with fumaric acid. Since these materials are nonvolatile, there no need to keep the reaction closed. Water created by this reaction is free to evaporate without altering the stoichiometric ratio of the starting materials.

In a 100 ml round bottom flask equipped with a magnetic stirbar, 10 g poly(propylene glycol), Mw 300, was added to 3.9 g fumaric acid. The flask was then submersed into a 180° C. oilbath and the mixture allowed to react for 2.5 hours. Similarly, 10 g poly(propylene glycol), Mw 600, was added to 1.9 g fumaric acid, and this mixture was allowed to react for 2.5 hours at 180° C.

The results of the reaction between non-volatile glycols, PPG 300 or 600 and PEG 300 or 600, are shown in Table 15.

TABLE 15

The Molecular Weight and Acid content as a function of the Reaction of fumaric acid and poly(propylene glycols)[a]

| molecular weight of poly(propylene glycol) | molecular weight (Mw/Mn) | acid content mmol COOH/g |
|---|---|---|
| 300 | 2044/446 | (insoluble in acetone) |
| 600 | 2828/615 | 0.83 |

[a] reacted for 2.5 hours at 180° C. under atmospheric pressure at a ratio of 1:1

By increasing the molecular weight of the poly(propylene glycol), the molecular weight of the resulting polymer is increased. The consistency of these polymers resembles a gel similar to the gel-like polymer formed from diethyl fumarate and PFP trimer. These polymers are barely soluble in acetone, and therefore are not well suited for biomedical purposes.

EXAMPLE 2

Step polymerization of PPF from PFP or MPM trimers

Preparation of PFP Pentamer

In a 1000 ml three neck round bottom flask equipped with a condenser and magnetic stirbar, 3 mol maleic anhydride is dissolved in 300 ml toluene. The flask is submerged into an oilbath kept at a constant 110° C. The mixture is allowed to come to reflux before 1 mol PFP trimer is slowly added using a pipette. The reaction is allowed to continue for 24 hours. At this time, the flask is removed from the oilbath and the mixture is transferred to a 1000 ml separatory funnel. After allowing the phases to distinctly separate, the lower phase is dissolved in ether while the upper toluene phase is discarded. Hexane is added to the ether mixture and the mixture set aside to facilitate separation of phases. The lower phase is transferred to a tared round bottom flask and rotary evaporated to remove excess solvents. The product is then lyophilized.

Preparation of PFP Heptamer

The procedure for making a heptamer is similar to that of making PFP trimer. However, since the starting materials are PFP pentamer and propylene oxide, both liquids, the reaction is homogeneous. 1 mol pentamer is dissolved in 4-methyl 2-pentanone. 3 ml pyridine is added at reflux, then excess propylene oxide is slowly dripped in. Since this reaction is homogeneous, less time, about 10 hours, is required to fully react the materials.

Preparation of PFP Nonamer

The procedure for preparing PFP nonamer is identical to that of the PFP pentamer. 3 mol maleic anhydride dissolved into toluene. One mol PFP heptamer is slowly added. This reaction is then allowed to continue for 24 hours.

Preparation of PFP 11-mer

The procedure for the preparation of PFP 11-mer is identical to that of PFP heptamer. 1 mol PFP nonamer is dissolved into 4-methyl 2-pentanone. 3 ml pyridine is added at reflux. Propylene oxide is slowly dripped into the reaction vessel. This reaction is allowed to continue for 10 hours.

The analysis of the oligomers synthesized in each step of the polymerization is described in Table 16.

TABLE 16

Analysis of Polymers formed by Step polymerization of PPF using PFP as starting material

| Oligo. | yield (%) | boil. point °C. | molecular weight | | | | acid con. mmol | | mech. stren. |
|---|---|---|---|---|---|---|---|---|---|
| | | | Mw | Mn | VPO | cal. mw | COOH/g | cal | MPa |
| trimer | 95.3 | 255 | 179 | 158 | 270 | 232 | 0 | 0 | 0 |
| pent | 88 | >300 | 338 | 319 | 400 | 428 | 4.78 | 4.67 | 1.73 |
| hept | 69 | >300 | 455 | 406 | 435 | 544 | 0 | 0 | 0 |
| non | 72.3 | >300 | 780 | 680 | 680 | 740 | 2.73 | 2.70 | 3.73 |
| 11 | 65 | >300 | 1277 | 1076 | 820 | 856 | 0 | 0 | 1.75 |

The molecular weights were determined by GPC and VPO. Neither determination is accurate since the error is large when a low molecular weight fragment is tested, however, a trend can be recognized. The acid content correlates perfectly with the calculated molecular weight. All fragments yield a single peak in the GPC chromatogram, indicating a pure compound. The mechanical strength is interesting: oligomers with acid end groups have higher mechanical strengths than oligomers with hydroxyl end groups. Additionally, increasing the molecular weight increases the mechanical strength.

Similar results are obtained from the step polymerization of the MPM trimer, shown in Table 17. The trimer demonstrates low mechanical strength, although it has a high content of acid end groups.

Preparation of MPM Pentamer

In a 1000 ml three neck round bottom flask equipped with a condenser and a magnetic stirbar, 1 mol MPM trimer is dissolved in 500 ml 4-methyl 2-pentanone. At reflux, 3 ml pyridine is added as a catalyst. Excess propylene oxide is slowly added dropwise through a dripping funnel. After 10 hours, the flask is removed from the oilbath. 300 ml 10% Na$_2$HPO$_4$ is added to the mixture which has been transferred to a 1000 ml separatory funnel. After vigorous shaking, the funnel is set aside to allow the phases to separate. The lower water phase is discarded while the upper phase containing the product is washed twice with 5% KCL solution. Again, the funnel is set aside to allow the phases to separate. The upper phase is then filtered through magnesium sulfate. The product is transferred to a tared round bottom flask and rotary evaporated. The product is then lyophilized to remove trace quantities of solvents.

Preparation of MPM Heptamer

The procedure for the preparation of MPM heptamer is similar to that of the MPM trimer, however, MPM pentamer is used as a starting material rather than propylene glycol. Three mol maleic anhydride is dissolved in toluene in a 1000 ml three neck round bottom flask equipped with a condenser and a magnetic stirbar. At reflux, 1 mol MPM pentamer is slowly added. The reaction is allowed to continue for 24 hours. The flask is then removed from the oilbath.

Preparation of MPM Nonamer

The procedure for the preparation of MPM is identical to that of MPM pentamer. 1 mol MPM heptamer is dissolved into methyl pentanone. At reflux, 3 ml pyridine is added. Propylene oxide is slowly added dropwise. The reaction continues for 10 hours.

Preparation of MPM 11-mer

The procedure for the preparation of MPM 11-mer is identical to that of MPM heptamer. 3 mol maleic anhydride is dissolved into toluene. At reflux, 1 mol MPM nonamer is slowly added. The reaction is allowed to proceed for 24 hours.

TABLE 17

Analysis of Polymers Synthesized by Step Polymerization of PPF using MPM as Starting Material

| Oligo. | yield (%) | molecular weight | | | acid con. mmol | | mech. stren. |
|---|---|---|---|---|---|---|---|
| | | Mw | Mn | cal | COOH/g | cal | MPa. |
| trimer | 98.9 | — | — | 272 | 5.63 | 6.12 | 0.43. |
| pentamer | 77.9 | 507 | 458 | 388 | 0 | 0 | 0 |
| heptamer | 66.4 | 620 | 570 | 584 | 3.56 | 3.42 | 2.4 |
| nonamer | 69.0 | 1271 | 879 | 700 | 0 | 0 | 0.55 |
| 11-mer | 64.6 | 1259 | 826 | 896 | 2.02 | 2.53 | 3.6 |

It is apparent that the mechanical strength of the polymer can be increased by increasing the number of acid end groups and increasing the molecular weight.

The elemental analysis for the oligomers is close to the calculated values, as demonstrated by the analysis in Table 18.

TABLE 18
Elemental Analysis of Products of Step Polymerizations

|  | calculated |  | found |  |
|---|---|---|---|---|
|  | % carbon | % hydrogen | % carbon | % hydrogen |
| PFP trimer ($C_{10}H_{16}O_6$) | 51.72 | 6.90 | 51.67 | 6.93 |
| PFP pentamer ($C_{18}H_{20}O_{12}$) | 50.47 | 4.67 | 51.20 | 5.20 |
| PFP heptamer ($C_{24}H_{32}O_{14}$) | 52.94 | 5.88 | 53.36 | 6.32 |
| PFP nonamer ($C_{32}H_{36}O_{20}$) | 51.89 | 4.86 | 52.10 | 5.20 |
| PFP 11-mer ($C_{38}H_{48}O_{22}$) | 53.27 | 5.61 | 53.39 | 5.75 |
| MPM trimer ($C_{11}H_{12}O_8$) | 48.53 | 4.41 | 48.43 | 4.41 |
| MPM pentamer ($C_{17}H_{24}O_{10}$) | 52.58 | 6.19 | 54.53 | 6.92 |
| MPM heptamer ($C_{25}H_{28}O_{16}$) | 51.37 | 4.79 | 51.59 | 4.99 |
| MPM nonamer ($C_{31}H_{40}O_{18}$) | 53.14 | 5.71 | 54.08 | 6.05 |
| MPM 11-mer ($C_{39}H_{44}O_{24}$) | 52.23 | 4.91 | 52.05 | 5.02 |

EXAMPLE 3

PPF production by controlled reaction between propylene glycol and fumaric acid

A. Two Step Reaction

High molecular weights are achieved in the synthesis of PPF using a controlled two step reaction, where a mixture of fumaric acid and propylene glycol (at ratio of 1:1 or 1:1.05) is first reacted at 130° C. for 10 hours, and then at 180° C. for 2 additional hours. Acid content is lower for the product of the two step polymerization, as shown in Table 19, indicating that higher molecular weight fragments are formed, and that less unreacted fumaric acid is present after reaction.

Preparation of PPF by the Two Step method

In a 1000 ml three neck round bottom flask equipped with an overhead mechanical stirrer, condenser and trap for collecting water, and a thermometer, 1.05 mol propylene glycol and 1 mol fumaric acid are combined. The flask is placed in a heating mantle at 130° C. The entire reaction apparatus is then wrapped with insulating material, and the reaction is started. The reaction is constantly stirred for 10 hours, and the temperature kept constant at 130° C. The contents of the flask should appear clear. The reaction temperature is then raised to 180° C. and the reaction continued for another 2 hours. A clear viscous liquid is obtained.

TABLE 19
Two Step Polymerization of PG and FA[a].

| Run No. | Molecular Weight[b] | Acid Content mole/g | Mech. Streng. MPa |
|---|---|---|---|
| A | 1645 | 548 | 1.34 | 21.6 |
| B | 1725 | 488 | 1.55 | 16.8 |
| C | 1281 | 521 | 1.21 | 18.7 |
| D | 1320 | 455 | 1.44 | 19.2 |

[a]PG and FA 1.05:1 were polymerized at 130° C. for 10 hours and at 180° C. for 2.0 hours at atmospheric pressure.
[b]The molecular weight of the polymers after the first step (10 hours at 130° C.) was $Mw \approx 450$ and $Mn \approx 250$.

B. Reaction in the presence of an azeotrope

PPF synthesized using xylene to form an azeotrope with the excess water in the reaction displays a high molecular weight, as demonstrated in Table 20. The PPF synthesized by this method is clear, colorless, of a desirable viscosity, and completely devoid of excess fumaric acid.

PG was reacted with FA in the presence of xylene, as follows: in a 1000 ml three neck round bottom flask equipped with an overhead mechanical stirrer, condenser and a trap, 1 mol fumaric acid is added to 1 mol propylene glycol. 0.25 ml sulfuric acid is added as a catalyst. PTSA may also be used. 100 ml xylene is added and the flask submersed into a >140° C. oilbath, where the reaction mixture is rapidly stirred. A two phase system of xylene and water is collected in the trap. The reaction is terminated when 18 ml water has collected in the trap (bottom phase), after 16 hours. The xylene remaining in the flask is decanted, and the reaction product, a clear colorless viscous liquid is extracted with hexane (2×300 ml). The polymer is then rotary evaporated to dryness using an oil pump (<0.1 mm Hg). The product is then analyzed for acid content and by GPC.

TABLE 20
Reaction of Fumaric Acid and Propylene Glycol with Xylenes[a].

| Ratio (FA:PG) | Catalyst | Molecular Weight Mw/Mn | Acid Content mmol COOH/g | Mech. Stren. |
|---|---|---|---|---|
| 1:1 | none | 551/313 | 1.03 | 4.7 |
| 1:1 | $H_2SO_4$ | 1550/587 | 1.58 | 19.8 |
| 1:1 | $H_2SO_4$ | 1450/525 | 1.54 | 17.6 |
| 1:1 | $H_2SO_4$ | 1632/625 | 1.47 | 18.2 |
| 1:1 | PTSA | 1642/613 | 1.44 | 16.8 |

[a]refluxing xylene with FA:PG 1:1 molar ratio for 16 hours.

EXAMPLE 4

Polymers with increased hydrolytic instability

Polylactide, if incorporated into polymers of MPM and PFP, will enhance its degradability. The lactide is first reacted with 1.0% antimony trifluoride for 6 hours at 140° C., or with MPM and PFP in the presence of antimony trifluoride. The ratio of PFP and MPM in the reaction is 1:1. If the product of this reaction is completely soluble in acetone, then the polyactide has been entirely incorporated into the polymer formed. The PFP/MPM mixture is then reacted at 180° C. for 3.5 hours. Copolymerization with glycolide or lactide is performed by reacting equal molar amounts of MPM and PFP trimers and various amounts of up to 95% lactide or glycolide.

A. Reaction of MPM, PFP and Lactide or Glycolide using antimony trifluoride as a catalyst Reactions were set up similarly for all samples. Each reaction was conducted for 22 hours at 140° C. and for an additional 2 hours at 220° C. under high vacuum. The reactions were conducted in a large test tube equipped with a small magnetic stirbar.

The ratios of MPM/PFP/lactide with 1% antimony trifluoride used were as follows:

1:1:1  2.72 g MPM, 2.32 g PFP, 1.44 g lactide, 0.014 g antimony trifluoride
1:1:2  2.72 g MPM, 2.32 g PFP, 2.88 g lactide, 0.029 g antimony -continued 1:1:4 2.72 g MPM, 2.32 g PFP, 5.76 g lactide, 0.058 g antimony trifluoride
1:1:8 2.72 g MPM, 2.32 g PFP, 11.52 g lactide, 0.115 g antimony trifluoride The ratios of MPM/PFP/glycolide with 1% antimony trifluoride used were as follows:

1:1:1 2.72 g MPM, 2.32 g PFP, 1.16 g glycolide, 0.012 g antimony trifluoride
1:1:2 2.72 g MPM, 2.32 g PFP, 2.32 g glycolide, 0.023 g antimony trifluoride
1:1:4 2.72 MPM, 2.32 g PFP, 4.64 g glycolide, 0.046 g antimony trifluoride
1:1:8 2.72 g MPM, 2.32 g PFP, 9.28 glycolide, 0.093 g antimony trifluoride These polymers were analyzed by GPC, acid content, melting point, IR and H[1]-NMR and for solubility. Since poly(lactide) is not soluble in acetone, ether or methanol and poly(glycolide) is insoluble in ether, chloroform (CHCl$_3$), acetone, tetrahydrofuran (THF), ethanol, methanol, toluene, and hexane, solubility can be used to demonstrate whether or not all the lactide or glycolide has been incorporated into the polymer.

TABLE 21

Solubility of Lactide containing Polymer.[a]

| sample | ether | CHCl$_3$ | acetone | THF | ethanol | methanol | toluene | hexane |
|---|---|---|---|---|---|---|---|---|
| 1:1:1 | −/+ | + | + | + | − | −/+[b,c] | +/− | − |
| 1:1:2 | −/+[b,c] | + | + | + | −/+ | +/−[b,c] | +/− | − |
| 1:1:4 | −/+[b] | +[b] | +[b] | + | +/−[b] | +[b] | +/− | − |
| 1:1:8 | +[b] | +[b] | +[b] | + | +[b,c] | + | +/− | − |

+ completely soluble
− completely insoluble
+/− mostly soluble
[a]after 22 hours at 140° C. and 2 hours at 220° C.
[b]white precipitate
[c]cloudy solution after vortexing

TABLE 22

Molecular weights of PFP-MPM-Lactide Copolymers

| | after 22 hours | | | after 24 hours | | | |
|---|---|---|---|---|---|---|---|
| sample | Mw | Mn | acid content | Mw | Mn | acid content | melt pt. |
| 1:1:1 | 3856 | 1335 | 1.02 | 8399 | 1669 | 0.18 | 54–56 |
| 1:1:2 | 2009 | 1070 | 1.43 | 5840 | 1778 | 0.25 | 46–48 |
| 1:1:4 | — | — | 1.44 | 2649 | 1045 | 0.51 | 35–38 |
| 1:1:8 | — | — | — | 1983 | 851 | 0.42 | 35–38 |

TABLE 23

Solubility of Glycolide containing samples

| sample | ether | CHCl$_3$ | acetone | THF | ethanol | methanol | toluene | hexane |
|---|---|---|---|---|---|---|---|---|
| 1:1:1* | − | +/− | −/+ | − | − | − | − | − |
| 1:1:2 | − | + | + | +/− | − | − | −/+ | − |
| 1:1:4 | − | +[a] | + | +/− | − | − | −/+ | − |
| 1:1:8 | − | +/−[b] | +/−[b] | +/−[b] | − | − | −/+ | − |

+ completely soluble
− completely insoluble
+/− mostly soluble
−/+ slightly soluble
[a]cloudy solution before vortexing
[b]white precipitate

TABLE 24

Molecular Weight of PFP-MPM-Glycolide Copolymers[a]

| | after 22 hours | | | after 24 hours | | | |
|---|---|---|---|---|---|---|---|
| sample | Mw | Mn | acid content | Mw | Mn | acid content | melt pt. |
| 1:1:1 | 4850 | 1027 | 0.80 | not soluble | | not soluble | |
| 1:1:2 | 3396 | 1062 | 0.68 | 4593 | 2151 | | |
| 1:1:4 | 1665 | 762 | 0.48 | 4255 | 1009 | | |
| 1:1:8 | 1652 | 591 | not soluble | 4588 | 627 | | |

[a]acid content and melting point were difficult to determine for these samples since the polymer was not easily soluble in chloroform and are very sticky.

Copolymers of 30 and 60% lactic acid are completely soluble in acetone and chloroform. The polymers are clear and uniform, indicating that the lactide has been entirely incorporated into the polymer structure.

When MPM and PFP trimers are reacted with lactide (1:1:1) for 90 minutes at 180° C. at atmospheric pressure, there is a rapid increase in molecular weight between 75 and 90 minutes of reaction: at 30 minutes, Mw/Mn is 371/213; at 45 minutes, Mw/Mn is 427/216; at 60 minutes, Mw/Mn is 513/259; at 75 minutes, Mw/Mn is 651/292; and at 90 minutes, Mw/Mn is 1759/574.

When MPM pentamer and PFP pentamer are reacted at a ratio of 1:1:1 for 90 minutes at 180° C., the molecular weights of the polymer are greater than those of the MPM/PFP trimer and lactide reaction: at 30 minutes, Mw/Mn is 577/275; at 45 minutes, Mw/Mn is 657/323; at 60 minutes, Mw/Mn is 820/351; at 75 minutes, Mw/Mn is 925/380; and at 90 minutes, Mw/Mn is 2009/466.

B. Incorporation of an Anhydride Bond 10 mm MPM was added to 30 mmol poly(4-vinylpyridine) in a 100 ml round bottom flask equipped with a magnetic stirbar. This mixture was dissolved into 25 ml chloroform. 10 mmol phosgene solution in toluene was added dropwise to the mixture. The reaction was allowed to stir for 3 hours at 25° C. under constant nitrogen flow. The reaction was terminated and the solids removed by suction filtration. The filtrate was rotary evaporated to remove excess solvent and the product was stored under refrigeration.

C. Other methods of preparing PPF

Other methods of preparing PPF include reacting citraconic acid and maleic anhydride with propylene glycol in a ratio of 1:1 for 24 hours at 140° C. 19.5 g propylene glycol are added to the appropriate amount of either maleic anhydride (24.5 g) or citraconic acid (32.5 g) in a 100 ml round bottom flask equipped with a magnetic stirbar and a dry condenser. The flask is then submersed in a 180° C. oilbath and allowed to react for 6 hours.

EXAMPLE 5

Preparation and characterization of the Mechanical Properties of PPF Bone Cement Composites PPF compositions for use in biomedical applications such as bone cements are prepared using methods known to those skilled in the art, with the exception of the PPF, as discussed in the Background of the Invention with respect to MMA and other reported bone cements containing PPF. Specifically, plaster of paris and other fillers are added to the liquid PPF to form a paste. The paste is applied to the area to be repaired where it is further polymerized to form a solid polymeric material. Methods for preparing and applying bone cements using a liquid polymeric material are known to those skilled in the art.

For characterization of bone cements made with these methods, PPF/MMA specimens were prepared in the following manner: PPF (6 g), and MMA (1 g) were thoroughly mixed at 37° C. until the PPF was completely dissolved in the MMA. The PPF/MMA mixture was then mixed with a crosslinking catalyst (0.25 g benzoyl peroxide) and the particulate phase, consisting of 7.5 g, 30–45 mesh, 355–600 micron diameter tricalcium phosphate (TCP) and 7.5 g medical grade calcium carbonate powder. Two drops of dimethyl-p-toluidine (DMT) was added to initiate crosslinking of the cement. The polymerizing PPF composite was then placed in cylindrical Teflon molds (6 mm round diameter×12 mm length) and allowed to harden at least 48 hours prior to mechanical testing.

Compressive testing for strength and modulus, using ASTM standard F451-76 for acrylic bone cement (6 mm round×12 mm length specimens), was conducted in an INSTRON 1331 materials test system interfaced to a MINC 11/03 laboratory computer. Uniaxial compression tests were conducted at a strain rate of 0.01/sec between two lubricated plates. Automated data acquisition techniques were used to obtain a computer generated x-y plot of stress versus strain from which compressive strength and modulus at 10% strain were computed. Raw data for load and deflection were obtained at a sampling rate of 25 Hz with sensitivities of 0.5N and 0.005 mm, respectively. A nonrecursive digital filter algorithm was used to reduce noise distortion. Compressive strengths were determined from the maximum loads achieved divided by the original cross-sectional area (approximately 28 mm$^2$). The modulus at each point was computed using the central difference method.

The biodegradation of these materials in vitro is tested by immersing the device in various liquids. For example, water causes a slight swelling of a PPF/MMA bone cement matrix and the specimens decrease in mechanical strength and stiffness. However, after a few days, secondary calcium ion reactions occur and the specimens return to their material properties. No evidence of degradation occurs. If PPF:MMA (85:15) samples are placed in an alkaline solution at pH 10 or greater, the specimens initially decrease in strength due to swelling of the polymer. However, they never regain their strength because the polymer degrades. Within a few days, the specimens can be easily crushed with the end of a pencil. If higher amounts of MMA are used, such as 70:30, then degradation does not occur and the specimens retain their material proerties. In fact, due to the secondary calcium ion effect, the materials actually become stronger. If specimens are placed in an acidic solution, the phosphate is very quickly leached out of the specimens. The material loses its stiffness but retains its shape due to the strength of the polymer, which is not degraded. There is little difference between specimens containing high or low concentrations of MMA monomer.

EXAMPLE 6

Application of PPF as a Tissue Adhesive or Controlled Release Device

All PPF polymers synthesized by these method are soluble in chloroform, methylene chloride, tetrahydrofuran, acetone, alcohol, and ethyl acetate. They are partially soluble in toluene, and not soluble in petroleum ether and water. The polymers with free carboxylic groups have good adhesiveness to hydrophilic surfaces such as body tissue and may therefore be useful as an adhesive or glue for raw surfaces, freshly cut tissue and traumatic tissue whether bleeding, wet or dry. In this application, the polymer would be applied as a paste, then crosslinked to form a compact solid seal.

Liver transplantation has become a successful therapeutic modality for end stage liver disease. However, there is a critical donor organ shortage in pediatric transplantation so that many children die while waiting for a donor organ. A potential solution to this problem is to use portions of a larger adult organ. This has been successfully tried in the United States. Unfortunately, a major problem is that the raw cut surface of the organ, without adequate sealing, leaks bile and blood, increasing the chance of infection. This is a potentially devastating complication in an immunosuppressed child.

The PPF made according to the methods of the present invention is useful in overcoming this problem. As demonstrated on a mouse liver, low molecular weight PPF can be applied and cross-linked with benzoyl peroxide-DMT to provide an immediate, complete seal. The polymer displays excellent adhesiveness to the raw tissue. The further advantage of the polymer is that it degrades as the wound heals.

EXAMPLE 7

PPF Controlled Drug Delivery Device

The polymeric material is also useful as a matrix for a compound to be released in a controlled fashion in vivo. The method of synthesis of the polymer is manipulated to produce a polymer degrading at a desired rate over a specified period of time. The most important advantage of this type of release is the avoidance of having to remove the drug depleted device.

In general, tissue adhesive or controlled release polymeric compositions according to the present invention may be either low or high molecular weight. Low molecular weight polymers are defined as having a Mw of about 500 to 3000 and a Mn of about 300 to 2000. High molecular weight is generally in the range of a Mn of 2000 to 100,000. Low molecular weight mixtures are applied with or without a catalyst in liquid or paste form and then crosslinked by radical polymerization or radiation. A radical source can be incorporated into the mixture such as benzoyl peroxide azobisisobutironitrile. The mechanical strength of the tissue adhesive or delivery device is usually not important. High molecular weight compounds are applied as a concentrated solution, about 5 to 40%, in a solvent such as acetone, ethyl acetate, or ethylene chloride. A crosslinking agent is not required since a hard polymeric matrix is left after the solvent is evaporated from the high molecular weight polymers.

Modifications and variations of this invention, methods for making and using poly(propyleneglycol fumarate) for biomedical applications will be obvious to those skilled in the art from the foregoing detailed description. Such modifications and variations are intended to come within the scope of the appended claims.

I claim:

1. A biodegradable, biocompatible polymeric composition useful for repair of bone or tissue comprising:
   polymers of fumaric acid and propylene glycol having a preferred weight average molecular weight (Mw) of between about 500 and 3000 and a number average molecular weight (Mn) of between about 300 and 2000, and between 1 and 2 mmole carboxylic acid end groups per gram of polymer.

2. The polymeric composition of claim 1 having between 1.3 and 1.6 mmole carboxylic end groups per gram of polymer.

3. The polymeric composition of claim 1 having a mechanical strength between 5 and 40 mPa.

4. The polymeric composition of claim 3 having a mechanical strength between 10 and 25 MPa.

5. A poly(propylene glycol fumarate) polymeric composition having a number average molecular weight between about 300 and 2000 and a weight average molecular weight between 500 and 3000 wherein said composition is produced by ester melt condensation from diacid monomers and glycols which do not evaporate under melt condensation conditions of 180° C.

6. The polymeric composition of claim 5 formed by melt condensation of a compound selected from the group consisting of fumaric acid, bis-propylene glycol fumarate, 1,2 propylene glycol dibutenoate, propylene glycol oligomers having a molecular weight range between 100 and 5000, ethylene glycol oligomers having a molecular weight between 100 and 5000, maleic acid, maleic anhydride, citraconic acid, citraconic anhydride, and oligomers thereof.

7. The polymeric composition of claim 6 comprising the reaction product of fumaric acid and a compound selected from the group consisting of bis-propylene glycol fumarate and MPM pentamer at a ratio of 0.65:1 wherein said product contains minimal unreacted acid and has high mechanical strength.

8. The polymeric composition of claim 6 comprising the reaction product of PFP and MPM trimers at a ratio of 1:1.

9. The polymeric composition of claim 6 comprising the reaction product of MPM and PFP trimers with a compound selected from the group consisting of lactic acid or glycolic acid, said composition having lactic acid linkages.

10. A polymeric composition formed by step polymerizing trimers selected from the group consisting of bis-propylene glycol fumerate trimer, 1,2 propylene glycol dibutenoate (BPB and and MPM) trimer to form pentamers having carboxyl end groups; step polymerizing the product thereof to form heptamers having hydroxyl end groups; repeating the reactions of oligomers having carboxyl end groups to form longer oligomers having hydroxyl end groups and of oligomers having hydroxyl end groups to form longer oligomers having carboxyl end groups until polymers having between 1 and 2 mmole carboxylic acid end groups per gram of polymer and weight average molecular weight of between 500 and 3000 and number average molecular weight between about 300 and 2000.

11. A polymeric composition having a number average molecular weight of between about 300 and 2000 and a weight average molecular weight between 500 and 3000 wherein said composition is produced in two steps, first by polymerizing fumaric acid and propylene glycol at a temperature of between about 100° and 140° C. until the fumaric acid and propylene glycol form short polymers having weight average molecular weight of between 300 and 1000 and number average molecular weight between 200 and 600, then condensing the short polymers at a temperature between greater than 140° C. and 180° C. to form polymers having a weight average molecular weight of between 500 and 3000 and number average molecular weight between about 300 and 2000.

12. A polymeric composition having a number average molecular weight of between about 300 and 2000 and a weight average molecular weight of between about 500 and 3000 wherein said composition is produced by polymerizing fumaric acid and propylene glycol in the presence of an azeotrope.

13. A method for producing a poly(propylene glycol fumarate) composition having a controlled number average molecular weight, narrow polydispersity with minimal low molecular weight fractions, and high reproducibility comprising:
   polymerizing by melt condensation compounds which do not evaporate under melt condensation conditions of 180° C. selected from the group consisting of bis-propylene glycol fumarate, oligomers of bis-propylene glycol fumarate, 1,2 propylene glycol dibutenoate, oligomers of 1,2 propylene glycol dibutenoate, oligomers of propylene glycol having a molecular weight range of between about 100 and 5000, and oligomers of ethylene glycol having a molecular weight range of between about 100 and 5000, with a compound selected from the group consisting of fumaric acid, oligomers of fumaric acid having carboxylic end groups, maleic acid, maleic anhydride, citraconic acid, and citraconic anhydride.

14. The method of claim 13 further comprising controlling the molecular weight, polydispersity, and end groups by controlling the ratio of reactants, polymerization time, and polymerization temperature.

15. The method of claim 14 wherein the molecular weight of the resulting polymer is increased by polymerizing oligomers having higher molecular weights than the trimers.

16. The method of claim 13 further comprising increasing the mechanical strength of the resulting polymer by increasing the number of carboxyl end groups in the resulting polymer.

17. The method of claim 16 wherein the mechanical strength of the resulting polymer in a bone cement composition is increased by polymerizing starting materials with a higher ratio of carboxyl end groups to hydroxyl end groups.

18. A method for producing poly(propylene glycol fumarate) having a controlled molecular weight, narrow polydispersity with minimal low molecular weight fractions, and high reproducibility comprising:
   (a) step polymerizing bis-propylene glycol fumarate (PFP) trimer with maleic anhydride to form pentamers having carboxyl end groups and step polymerizing 1,2 propylene glycol dibutenoate (BPB and MPM) trimer with propylene oxide to form pentamers having hydroxyl end groups;
   (b) step polymerizing the pentamers formed by the reaction of bis-propylene glycol fumarate with maleic anhydride with propylene oxide to form heptamers having hydroxyl end groups and step polymerizing the pentamers formed by the reaction of 1,2 propylene glycol dibutenoate trimer with propylene oxide to form heptamers having carboxyl end groups;
   (c) step polymerizing heptamers formed by the reaction of the pentamers having hydroxyl end groups with maleic anhydride to form nonamers having carboxyl end groups and step polymerizing the heptamers formed by the reaction of the pentamers having the carboxyl end groups with propylene oxide to form nonamers having hydroxyl end groups; and
   (d) repeating the step polymerization of polymers having carboxyl end groups with propylene oxide to form longer polymers having hydroxyl groups and of polymers having hydroxyl groups with maleic anhydride to form longer polymers having carboxyl groups until polymers having between 1 and 2 mmole carboxylic acid end groups per gram of polymer and weight average molecular weight of between 500 and 3000 and number average molecular weight between about 300 and 2000.

19. A method for producing poly(propylene glycol fumarate) having a controlled molecular weight, narrow polydispersity with minimal low molecular weight fractions, and high reproducibility comprising:
   (a) polymerizing by melt condensation fumaric acid and propylene glycol at a temperature between about 100° C. and 140° C. for approximately 10 to 20 hours until polymers having a weight average molecular weight between 300 and 1000 and a number average molecular weight between 200 and 600 are formed; and
   (b) polymerizing by melt condensation the product step (a) at a temperature between greater than 140° C. to approximately 180° C. for about one to two hours until poly(propylene glycol fumarate) having weight average molecular weight of between 500 and 3000 and number average molecular weight between about 300 and 2000 is formed.

20. The method of claim 19 wherein the closed system contains a trap to collect the water produced in the reaction between the fumaric acid and the propylene glycol.

21. The method of claim 19 wherein the reactants are fumaric acid and propylene glycol at a ratio of between about 1:1 and 1:1.1.

22. A method for producing poly(propylene glycol fumarate) having a controlled molecular weight, narrow polydispersity with minimal low molecular weight fractions, and high reproducibility comprising:
   polymerizing in a closed system mixture of fumaric acid and propylene glycol in the presence of an azeotrope to remove the water produced by the reaction until polymers having weight average molecular weight of between 500 and 3000 and number average molecular weight between about 300 and 2000 are produced.

23. The method of claim 22 wherein the azeotrope is xylene and the fumaric acid and propylene glycol are reacted in a closed system with a water collecting trap at reflux conditions for approximately 10 to 20 hours.

24. A method for producing a biodegradable poly(propylene glycol fumarate) polymer having increased susceptibility to hydrolysis comprising
   polymerizing MPM and PFP trimers with a compound selected from the group consisting of lactic acid or glycolic acid to form copolymers having lactic acid linkages until polymers having weight average molecular weight of between 500 and 3000 and number average molecular weight between about 300 and 2000 are produced.

25. The method of claim 24 further comprising reacting the trimers at a ratio of MPM:PFP of 1:1.

26. The method of claim 24 further comprising reacting the trimers in the presence of a catalyst.

27. The method of claim 24 comprising reacting the trimers with a compound selected from the group consisting of lactic acid or glycolic acid to form copolymers having lactic acid linkages.

28. A method for repairing damage to tissue or bone comprising applying a polymeric composition of fumaric acid and propylene glycol having a range of number average molecular weights between about 500 and 3000 and between 1 and 2 mmole carboxylic acid end groups per gram of polymer, and crosslinking the applied polymeric composition.

29. The method of claim 28 further comprising incorporating a radical source for crosslinking into the polymeric composition.

30. A method for forming biocompatible, biodegradable implants comprising selecting a polymeric composition formed of fumaric acid and propylene glycol having a range of number average molecular weights between about 2000 and 100,000, dissolving the polymeric composition in a solvent at a concentration of between about 5 to 40% polymer in combination with a crosslinking agent, applying the solution and removing the solvent, and crosslinking.

31. The polymeric composition of claim 1 for bone repair comprising:
   approximately 5 to 40% poly(propylene glycol fumarate);
   approximately 0 to 15% monomer selected from the group consisting of vinyl monomer, methacrylic acid, acrylic acid, alkyl esters of methacrylic acid, alkyl esters of acrylic acid, vinyl pyrrolidone, and vinyl acetate;
   approximately 45 to 90% filler selected from the group consisting of calcium slats, calcium carbonate, calcium sulfate, plaster of paris, hydroxy apatite, and bone; and
   a free radical initiator selected from the group consisting of benzoylperoxide, t-butyl hydroperoxide, methyl ethyl ketone peroxide, t-butyl perbenzoate, and an accelerator selected from the group consisting of N,N-dimethyl toludine and cobalt naphthanate.

32. The polymeric composition of claim 31 further comprising polymers of the poly(propylene glycol fumarate) and hydroxy acids selected from the group consisting of lactic acids, glycolic acid, and glycols.

33. The polymeric composition of claim 31 comprising approximately 45 to 90% filler.

34. The composition of claim 1 further comprising a drug.

35. The method of claim 30 further comprising adding a drug to the polymeric composition.

36. The composition of claim 31 further comprising a drug.

* * * * *

UNITED STATES PATENT AND TRADEMARK OFFICE
CERTIFICATE OF CORRECTION

PATENT NO. : 4,888,413
DATED : December 19, 1989
INVENTOR(S) : Domb

It is certified that error appears in the above-identified patent and that said Letters Patent is hereby corrected as shown below:

Column 26, line 14, insert --tricalcium-- before "phosphate".
Column 28, line 5, insert --(PFP)-- before "trimer".
Column 30, line 5, insert --a-- before "mixture".

Signed and Sealed this

Sixteenth Day of July, 1991

Attest:

HARRY F. MANBECK, JR.

Attesting Officer

Commissioner of Patents and Trademarks